United States Patent
Maruta et al.

(10) Patent No.: US 12,274,576 B2
(45) Date of Patent: Apr. 15, 2025

(54) RADIOGRAPHIC IMAGE CAPTURING DEVICE, RADIOGRAPHIC IMAGE CAPTURING SYSTEM, CONTROL METHOD, AND CONTROL PROGRAM

(71) Applicant: Konica Minolta, Inc., Tokyo (JP)

(72) Inventors: Yuuichi Maruta, Hino (JP); Hiroaki Nakano, Sagamihara (JP)

(73) Assignee: Konica Minolta, Inc., Tokyo (JP)

( * ) Notice: Subject to any disclaimer, the term of this patent is extended or adjusted under 35 U.S.C. 154(b) by 250 days.

(21) Appl. No.: 17/518,948

(22) Filed: Nov. 4, 2021

(65) Prior Publication Data

US 2022/0175336 A1 Jun. 9, 2022

(30) Foreign Application Priority Data

Dec. 3, 2020 (JP) .................................. 2020-201120

(51) Int. Cl.
*A61B 6/00* (2024.01)
*A61B 6/46* (2024.01)

(52) U.S. Cl.
CPC ................ *A61B 6/54* (2013.01); *A61B 6/461* (2013.01); *A61B 6/5258* (2013.01); *A61B 6/56* (2013.01)

(58) Field of Classification Search
CPC ......... A61B 6/4494; A61B 6/461; A61B 6/54; A61B 6/548; A61B 6/566; A61B 6/563; A61B 6/56; G16H 40/67; G16H 40/63; G16H 40/60
See application file for complete search history.

(56) References Cited

U.S. PATENT DOCUMENTS

| | | | |
|---|---|---|---|
| 6,806,487 B2* | 10/2004 | Tamakoshi | H04N 1/32529 250/586 |
| 10,684,237 B2* | 6/2020 | Graf | A61B 6/54 |
| 2006/0122481 A1* | 6/2006 | Sievenpiper | G16H 40/40 600/407 |
| 2007/0004980 A1* | 1/2007 | Warner | G01S 7/52017 600/411 |
| 2007/0022377 A1* | 1/2007 | Haider | A61B 6/545 715/707 |

(Continued)

FOREIGN PATENT DOCUMENTS

| | | |
|---|---|---|
| JP | 2011-62425 A | 3/2011 |
| JP | 2013-59654 A | 4/2013 |

(Continued)

OTHER PUBLICATIONS

Japanese Office Action (JPOA) mailed Jun. 25, 2024 and issued in Japanese Patent application No. 2020-201120 and its English machine translation.

*Primary Examiner* — Dani Fox
*Assistant Examiner* — Soorena Kefayati
(74) *Attorney, Agent, or Firm* — RANKIN, HILL & CLARK LLP

(57) ABSTRACT

A radiographic image capturing device connectable to a plurality of types of radiographic image capturing control devices having different specifications, includes a hardware processor that controls an operation of the radiographic image capturing device based on information indicating specifications or a type of a radiographic image capturing control device connected to the radiographic image capturing device.

20 Claims, 3 Drawing Sheets

(56) References Cited

U.S. PATENT DOCUMENTS

| | | | | |
|---|---|---|---|---|
| 2007/0146130 A1* | 6/2007 | Hannemann | | A61B 6/512 340/539.22 |
| 2008/0058963 A1* | 3/2008 | Garibaldi | | A61B 8/5238 700/19 |
| 2010/0080437 A1* | 4/2010 | Yoshida | | A61B 6/4464 340/600 |
| 2010/0208970 A1* | 8/2010 | Hattori | | A61B 6/4494 250/394 |
| 2011/0122995 A1* | 5/2011 | Ferro, Jr. | | G16H 40/67 378/62 |
| 2011/0150182 A1* | 6/2011 | Omura | | A61B 6/4405 378/116 |
| 2011/0178359 A1* | 7/2011 | Hirschman | | G21G 4/08 600/4 |
| 2011/0222657 A1* | 9/2011 | Kobayashi | | A61B 6/56 378/62 |
| 2012/0010475 A1* | 1/2012 | Rossmeier | | A61B 6/463 600/301 |
| 2012/0130238 A1* | 5/2012 | Muraoka | | A61B 6/4233 600/436 |
| 2012/0133601 A1* | 5/2012 | Marshall | | G06F 3/041 345/173 |
| 2012/0256920 A1* | 10/2012 | Marshall | | A61B 6/0414 345/420 |
| 2012/0291097 A1* | 11/2012 | Jones | | G06F 3/04847 726/3 |
| 2013/0058554 A1* | 3/2013 | Battle | | G16H 30/20 382/131 |
| 2013/0088452 A1* | 4/2013 | Glaser-Seidnitzer | | G06F 3/0488 345/173 |
| 2013/0102245 A1* | 4/2013 | Ohguri | | A61B 6/548 455/39 |
| 2013/0232432 A1* | 9/2013 | Liu | | A61B 6/548 715/771 |
| 2013/0279661 A1* | 10/2013 | Tamura | | A61B 6/42 378/114 |
| 2014/0140634 A1* | 5/2014 | Hayashida | | A61B 6/548 250/336.1 |
| 2014/0188515 A1* | 7/2014 | Mansker | | G16H 30/20 705/3 |
| 2014/0254758 A1* | 9/2014 | Saigusa | | A61B 6/548 378/62 |
| 2014/0254769 A1* | 9/2014 | Chicchetti | | A61B 6/563 378/204 |
| 2015/0039336 A1* | 2/2015 | Mayer | | A61B 5/0059 705/2 |
| 2015/0080701 A1* | 3/2015 | Hausotte | | G06T 7/0014 600/407 |
| 2016/0217684 A1* | 7/2016 | Bossier | | G08C 17/02 |
| 2016/0228087 A1* | 8/2016 | Oda | | A61B 6/5211 |
| 2016/0310099 A1* | 10/2016 | Hamano | | A61B 6/563 |
| 2017/0164916 A1* | 6/2017 | Kosuge | | A61B 6/465 |
| 2017/0164917 A1* | 6/2017 | Joerger | | A61B 6/5211 |
| 2017/0281113 A1* | 10/2017 | Tanaka | | A61B 6/4452 |
| 2017/0360390 A1* | 12/2017 | Tajima | | A61B 6/548 |
| 2018/0021006 A1* | 1/2018 | Takasawa | | G16H 40/60 378/116 |
| 2018/0144823 A1* | 5/2018 | Raman | | H04L 67/55 |
| 2019/0159746 A1* | 5/2019 | Hikosaka | | A61B 6/465 |
| 2019/0313996 A1* | 10/2019 | Park | | A61B 6/5294 |
| 2020/0029921 A1* | 1/2020 | Pickert | | A61B 6/563 |
| 2020/0041670 A1* | 2/2020 | Ishioka | | A61B 6/4266 |
| 2020/0242815 A1* | 7/2020 | Szczykutowicz | | G06T 11/005 |
| 2021/0093285 A1* | 4/2021 | Hader | | G16H 40/63 |
| 2021/0117207 A1* | 4/2021 | Berreth | | A61B 8/565 |
| 2021/0169435 A1* | 6/2021 | Nonaka | | A61B 6/4233 |

FOREIGN PATENT DOCUMENTS

| | | |
|---|---|---|
| JP | 2015008832 A | 1/2015 |
| JP | 2015058342 A | 3/2015 |
| JP | 2016147044 A | 8/2016 |
| JP | 2019-17441 A | 2/2019 |
| WO | 2006101230 A1 | 9/2006 |

* cited by examiner

RADIOGRAPHIC IMAGE CAPTURING DEVICE, RADIOGRAPHIC IMAGE CAPTURING SYSTEM, CONTROL METHOD, AND CONTROL PROGRAM

The entire disclosure of Japanese patent Application No. 2020-201120, filed on Dec. 3, 2020, is incorporated herein by reference in its entirety.

BACKGROUND

Technological Field

The present invention relates to a radiographic image capturing device, a radiographic image capturing system, a control method, and a control program.

Description of the Related art

In recent years, a portable radiographic image capturing device such as a flat panel detector (FPD) is generally known as a radiographic image capturing device that acquires medical radiographic images. Even in a case where a plurality of radiographic image capturing systems are introduced in the same facility, using such a radiographic image capturing device enables the systems to share one radiographic image capturing device.

For example, JP 2011-62425 A discloses a radiographic image capturing system capable of easily and quickly associating a radiographic image capturing device with a radiographic image capturing control device corresponding to an image capturing room as a destination even when the radiographic image capturing device moves among a plurality of image capturing rooms corresponding to systems.

In addition, JP 2013-59654 A discloses a configuration in which a console makes it possible to determine whether the type of a cassette is a portable FPD cassette or a computed radiography (CR) cassette.

Furthermore, JP 2019-17441 A discloses a configuration in which, in a radiographic image capturing system including an FPD, the processing performance of the FPD and the processing performance of an external terminal paired with the FPD are determined, and whether image processing is executed by the FPD or the external terminal is determined according to a determination result.

Meanwhile, in recent medical device development, cooperation between companies (business to business (B to B)) has increased. For this reason, the use of a multi-vendor radiographic image capturing system has increased, which means, for example, a manufacturer of a radiographic image capturing device is different from a manufacturer of a radiographic image capturing control device.

In this case, when the manufacturer of the radiographic image capturing control device (radiographic image capturing system) develops a system having unique system specifications, the manufacturer of the radiographic image capturing device as a cooperation partner needs to manufacture the radiographic image capturing device having specifications in accordance with the specifications of the system.

Therefore, in a case where a plurality of types of radiographic image capturing control devices having different specifications coexist in the same facility, there is a problem that one radiographic image capturing device cannot be easily shared.

JP 2011-62425 A and JP 2013-59654 A do not mention that the specifications of the radiographic image capturing control devices are different, and thus a configuration in which one radiographic image capturing device is shared among a plurality of systems achieves improvement.

SUMMARY

An object of the present invention is to provide a radiographic image capturing device, a radiographic image capturing system, a control method, and a control program capable of easily sharing the radiographic image capturing device among a plurality of types of radiographic image capturing systems.

To achieve the abovementioned object, according to an aspect of the present invention, a radiographic image capturing device connectable to a plurality of types of radiographic image capturing control devices having different specifications, reflecting one aspect of the present invention comprises a hardware processor that controls an operation of the radiographic image capturing device based on information indicating specifications or a type of a radiographic image capturing control device connected to the radiographic image capturing device.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Figure 1:
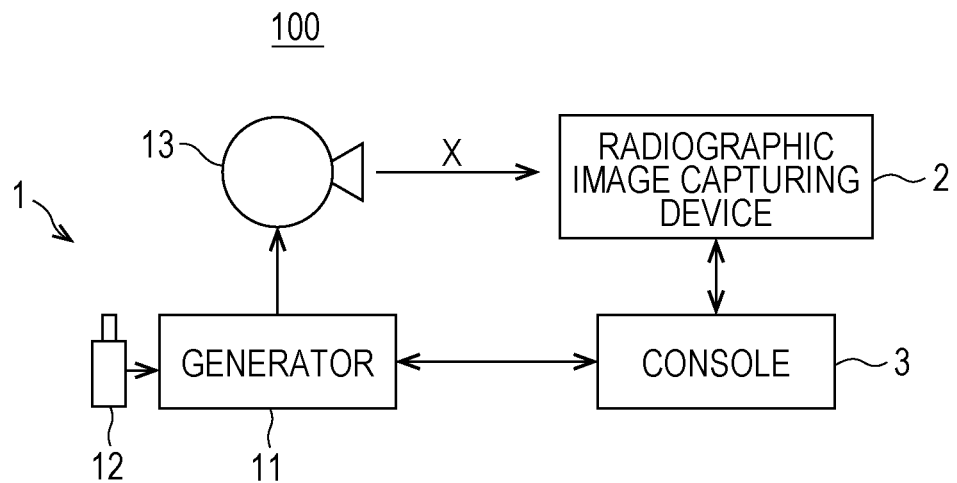
FIG. 1 is a block diagram illustrating a configuration of a radiographic image capturing system according to an embodiment of the present invention.

Hereinafter, one or more embodiments of the present invention will be described with reference to the drawings. However, the scope of the invention is not limited to the disclosed embodiments. FIG. 1 is a block diagram illustrating a configuration of a radiographic image capturing system 100 according to an embodiment of the present invention.

As illustrated in FIG. 1, the radiographic image capturing system 100 according to the present embodiment includes a radiation irradiation device 1, a radiographic image capturing device 2, and a console 3. In addition, the radiographic image capturing system 100 is connectable to a radiology information system (RIS), a picture archiving and communication system (PACS), and the like, which are not illustrated.

The radiation irradiation device 1 is connected to the console 3 so as to be able to communicate therewith in a wired or wireless manner. The radiation irradiation device 1 includes a generator 11, an exposure switch 12, and a radiation source 13.

The generator 11 is configured to be able to apply a voltage corresponding to preset radiation exposure conditions (such as a tube voltage, a tube current, an irradiation time, and a tube current time product (mAs value)) to the radiation source 13 based on an operation of the exposure switch 12.

The radiation source 13 (tube bulb) includes a rotating anode, a filament, and the like, which are not illustrated. When a voltage is applied from the generator 11, the filament irradiates the rotating anode with an electron beam corresponding to the applied voltage, and the rotating anode generates a radiation X (such as an X-ray) of a dose corresponding to the intensity of the electron beam.

Note that, although FIG. 1 illustrates the generator 11, the exposure switch 12, and the radiation source 13, which are separated, these may be integrally configured. In addition, FIG. 1 illustrates an example in which the exposure switch 12 is connected to the generator 11, but the exposure switch 12 may be provided in another device. Furthermore, the radiation irradiation device 1 may be installed in an image capturing room or may be configured to be movable by being incorporated in a medical cart or the like.

The radiographic image capturing device 2 is a portable device such as a flat panel detector (FPD), and is connected to the console 3 so as to be able to communicate therewith in a wired or wireless manner. The radiographic image capturing device 2 is configured to be able to generate image data of a radiographic image of a subject by being exposed to the radiation X from the radiation irradiation device 1 via the subject.

Figure 2:
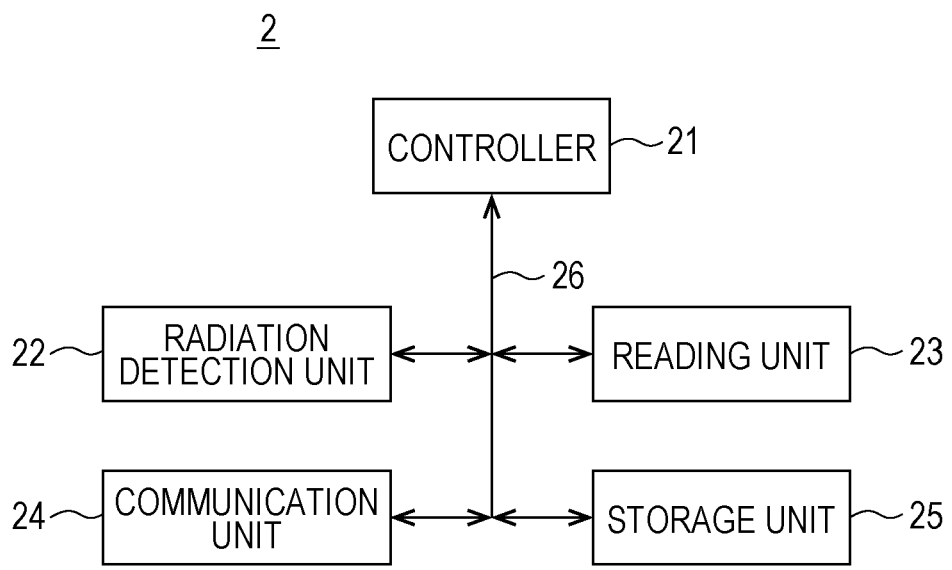
FIG. 2 is a block diagram illustrating a configuration of a radiographic image capturing device.

As illustrated in FIG. 2, the radiographic image capturing device 2 includes a controller 21, a radiation detection unit 22, a reading unit 23, a communication unit 24, a storage unit 25, and a bus 26 that connects the units.

The controller 21 includes a central processing unit (CPU), a random access memory (RAM), and the like. The CPU of the controller 21 reads various programs stored in the storage unit 25 based on reception of a control signal or the like from an external device such as the console 3, develops the programs in the RAM, executes various types of processing in accordance with the developed programs, and centrally controls an operation of each unit in the radiographic image capturing device 2.

The radiation detection unit 22 includes a substrate in which pixels each including a switch element and a radiation detection element that is exposed to the radiation X to generate a charge corresponding to the dose of the radiation X are arranged two-dimensionally (in a matrix).

The reading unit 23 is configured to be able to read the amount of charge emitted from each pixel as a signal value and generate the image data from the plurality of signal values.

The communication unit 24 is configured to be able to receive (acquire) various control signals, various types of data, and the like from an external device, and transmit various control signals, the generated image data, and the like to an external device.

The storage unit 25 includes a nonvolatile semiconductor memory, a hard disk, and the like, and stores various programs executed by the controller 21, parameters necessary for execution of processing by the programs, and the like. Furthermore, the storage unit 25 can store the image data generated by the reading unit 23 and various types of data processed by the controller 21.

When exposed to the radiation in a state where the controller 21 turns off each switch element of the radiation detection unit 22, the radiographic image capturing device 2 configured as described above accumulates the charge corresponding to the dose of the radiation in each pixel. When the controller 21 turns on each switch element and the charge is discharged from each pixel, the reading unit 23 converts the amount of each charge into a signal value and reads the signal values as the image data.

Note that the radiographic image capturing device 2 may incorporate a scintillator or the like, convert the applied radiation X into light of another wavelength such as visible light by the scintillator, and generate a charge corresponding to the converted light, or may generate a charge directly from the radiation X without interposing the scintillator or the like.

The console 3 includes a personal computer (PC), a mobile terminal, or a dedicated device, and is connected to the radiation irradiation device 1, the radiographic image capturing device 2, and the like so as to be able to communicate therewith in a wired or wireless manner. The console 3 can set image capturing conditions of the radiation irradiation device 1 and the radiographic image capturing device 2, a part to be captured by the radiation irradiation device 1 and the radiographic image capturing device 2, and the like based on an image capturing order from an external device (RIS or the like) or an operation by a user. The console 3 corresponds to a "radiographic image capturing control device" of the present invention.

Figure 3:
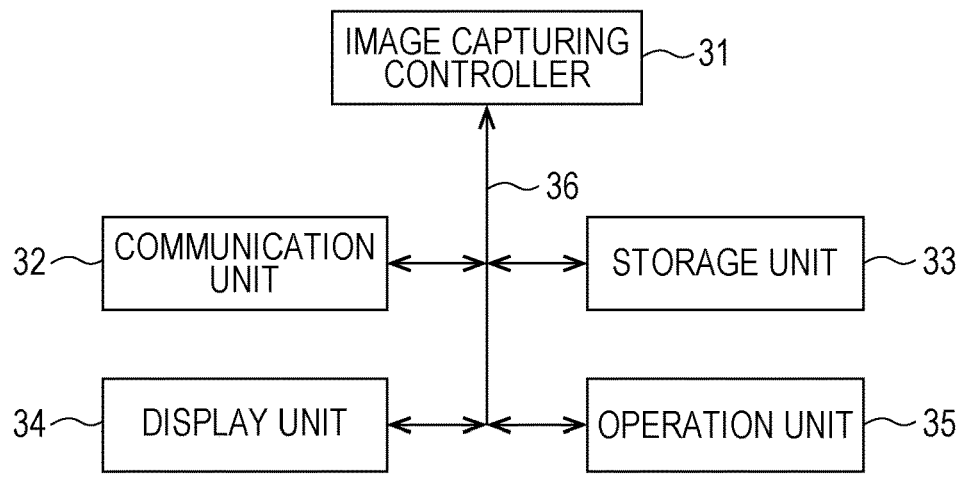
FIG. 3 is a block diagram illustrating a configuration of a console.

As illustrated in FIG. 3, the console 3 includes an image capturing controller 31, a communication unit 32, a storage unit 33, a display unit 34, an operation unit 35, and a bus 36 that connects the units.

The image capturing controller 31 includes a CPU, a RAM, and the like. The CPU of the image capturing controller 31 reads various programs stored in the storage unit 33 in response to an operation of the operation unit 35, develops the programs in the RAM, executes various types of processing in accordance with the developed programs, and centrally controls an operation of each unit of the console 3.

The communication unit 32 includes a local area network (LAN) adapter, a modem, a terminal adapter (TA), and the like, and controls transmission and reception of data to and from each device connected to a communication network.

The storage unit 33 includes a nonvolatile semiconductor memory, a hard disk, and the like, and stores various programs executed by the image capturing controller 31, parameters necessary for execution of processing by the programs, and the like. The storage unit 33 can store the image data received from the radiographic image capturing device 2 and the image data processed by the image capturing controller 31 in association with supplementary information.

The display unit 34 includes a monitor such as a liquid crystal display (LCD) or a cathode ray tube (CRT), and displays an input instruction, data, and the like from the operation unit 35 in accordance with an instruction of a display signal input from the image capturing controller 31.

The operation unit 35 includes a keyboard including cursor keys, numeric input keys, various function keys, and the like, and a pointing device such as a mouse, and outputs, to the image capturing controller 31, an instruction signal input by a key operation on the keyboard or a mouse operation. In addition, the operation unit 35 may include a touch panel on a display screen of the display unit 34, and in this case, outputs an instruction signal input via the touch panel to the image capturing controller 31.

Next, control of the radiographic image capturing device 2 according to the present embodiment will be described. The radiographic image capturing device 2 is portable as described above. For example, in a case where a plurality of radiographic image capturing systems 100 (installed in an image capturing room or incorporated in a medical cart) are in the same facility, the radiographic image capturing device 2 is configured to be movable among the plurality of systems.

The radiographic image capturing device 2 is configured to be connectable to a plurality of types of consoles 3 having different specifications, and is configured to be compatible with respective functions of the plurality of types of consoles 3. That is, even in a case where the plurality of types of consoles 3 having different specifications coexist in the same facility, the radiographic image capturing device 2 is configured to be able to be shared among the systems in which the respective consoles 3 are installed.

Having different specifications means that at least one of the functions of the plurality of types of consoles 3 or settings of the functions is different. Examples of the functions include an image capturing method of the radiographic image capturing device 2, an output method for various files, an image processing method, settings related to a user interface, and settings related to the system. Note that the functions of the consoles 3 may be other than those described above.

Being connectable to the plurality of types of consoles 3 means that the radiographic image capturing system 100 can perform an image capturing operation by connecting the radiographic image capturing device 2 to any one of the plurality of types of consoles 3.

Being compatible with the respective functions of the plurality of types of consoles 3 means that changing the above settings in the radiographic image capturing device 2 and using the radiographic image capturing device 2 make it possible to exhibit all the functions of the consoles 3 defined by a manufacturer of the radiographic image capturing control device (radiographic image capturing system) as specifications of the system including the radiographic image capturing device 2.

The controller 21 controls an operation of the radiographic image capturing device 2 based on information indicating the specifications or type of the console 3 connected to the radiographic image capturing device 2. The operation of the radiographic image capturing device 2 indicates activation and termination, image capturing, image correction and image processing at the time of image capturing, calibration for maintenance, and the like of the radiographic image capturing device 2. The information related to the type of the console 3 is, for example, at least one of information related to a manufacturer of the console 3, information related to a model of the console 3, or information related to software used in the console 3. The information related to the manufacturer is mainly intended to indicate information for determination, for example, in a case where the radiographic image capturing device 2 moves between a console of a predetermined first manufacturer and a console of a second manufacturer as a cooperation partner of the first manufacturer. The information related to the model of the console 3 is information related to a medical cart, a PC, a mobile terminal, or a dedicated device. The information related to the software used in the console 3 also includes information related to a version of the software. The information related to the model of the console 3 and the information related to the software used in the console 3 are mainly intended to indicate information for determination in a case where the radiographic image capturing device 2 is shared not only between the console of the first manufacturer and the console of the second manufacturer but also between consoles as different products (radiographic image capturing systems) of the first manufacturer.

The controller 21 acquires the information indicating the specifications or type of the console 3 to which the radiographic image capturing device 2 is connected from the console 3 via the communication unit 24, and determines one type of console 3 among the plurality of types of consoles 3 based on the acquired information. That is, the controller 21 determines which one of the consoles 3 the connected console 3 is based on the information indicating the specifications or type of the console 3. The controller 21 corresponds to a "determiner" of the present invention.

Examples of the information indicating the specifications or type of the console 3 include information on the manufacturer of the console 3, the software installed in the console 3, the model of the console 3, or the like. The controller 21 acquires identification information identifiable as the information indicating the specifications or type of the console 3 from, for example, the storage unit 33 of the console 3, and determines the specifications or the type of the console 3. As the identification information, the above-described various types of information may be defined in advance by codes, and the radiographic image capturing device 2 may be notified of the codes.

Note that the information indicating the specifications or type of the console 3 may be stored in the storage unit 25 of the radiographic image capturing device 2, or may be acquired by the controller 21 from the identification information stored in a peripheral device, an accessory, or the like of the radiographic image capturing system 100. The acquisition from the peripheral device indicates, for example, a method such as arranging an integrated circuit (IC) capable of storing the identification information in a head portion of a wired cable connected to the radiographic image capturing device 2 and reading the information in the IC at a connection timing As the acquisition from the peripheral device, a method is also conceivable in which the information is read from an IC provided in a charger of the radiographic image capturing device 2 connected in the system including the console to be determined at a timing when the charger is connected. As the acquisition from the peripheral device, a method of reading the identification information using a non-contact device may also be used. The acquisition from the accessory is similar to the acquisition from the peripheral device in the object and means, but a portable option for separately notifying the radiographic image capturing device 2 of the identification information without using the peripheral device fixed in the system may be separately prepared.

The controller 21 controls the operation of the radiographic image capturing device 2 according to a determination result (type) of the console 3.

For example, the controller 21 performs control to switch the image capturing method of the radiographic image capturing device 2 depending on the console 3 to which the radiographic image capturing device 2 is connected. More specifically, for example, in a case where the plurality of consoles 3 have different settings of the image capturing method of the radiographic image capturing device 2 and the console 3 to which the radiographic image capturing device 2 is connected is switched, the controller 21 performs control to switch the settings of the image capturing method of the radiographic image capturing device 2.

Examples of the settings of the image capturing method of the radiographic image capturing device 2 include settings related to error processing and settings of an exposure method in the radiographic image capturing system 100.

The settings related to the error processing indicate error processing or settings related to error processing. The error processing includes error processing related to a network connection determination method, error processing related to exposure control (delay setting of exposure response or the like), and the like in the radiographic image capturing system 100.

Examples of the exposure method in the radiographic image capturing system 100 include a cooperation method between the radiation irradiation device 1 and the radiographic image capturing device 2. Examples of the cooperation method include a method performed by software and a method performed by hardware. The cooperation mentioned here indicates reception of an irradiation start signal from the radiation irradiation device 1 and transmission of an interlock release signal from the radiographic image capturing device 2 to the radiation irradiation device 1. These signals may be exchanged as hardware signals or may be exchanged based on communication commands by software depending on specifications of the radiation irradiation device. Switching between these methods enables various systems to share the radiographic image capturing device 2.

The above-described settings of the image capturing method in the radiographic image capturing system 100 are different depending on the type of the console 3. In particular, regarding the error processing, the concept of what state the user is notified of as an error is different for each manufacturer, and thus, settings regarding a type of error content, a logic of error determination, a threshold of error determination, and error output specifications are often different depending on the type of the console 3. For example, in the case of an error caused by a drop or impact of the radiographic image capturing device 2, it is assumed that from what level of the drop or impact the user is notified, definitions of levels of "Information", "Caution", and "Warning" in a user notification method, and an algorithm for calculating the level of the drop or impact are different. In addition, it is conceivable to match the error output specifications of the radiographic image capturing device 2 with input specifications of the console 3, which receives information as an error output.

In the present embodiment, the settings of the image capturing method are switched depending on the console 3 to which the radiographic image capturing device 2 is connected, so that it is possible to maximize a unique function of the radiographic image capturing system 100 in which the radiographic image capturing device 2 is used.

Furthermore, the controller 21 performs control to switch the output method for various files depending on the console 3 to which the radiographic image capturing device 2 is connected. More specifically, for example, in a case where the plurality of consoles 3 have different settings of the output method for various files and the console 3 to which the radiographic image capturing device 2 is connected is switched, the controller 21 performs control to switch the settings of the output method for various files.

Examples of the output method for the files include encryption schemes of various files (such as image data, a file related to log data, a setting file, a file related to data used for image processing and image correction, and a file related to a map of defective pixels), formats of various files, use timings of various files, storage locations of various files, and communication specifications for transfer of various files. Data to be encrypted and an encryption scheme thereof are also changed for each manufacturer in many cases.

The above-described settings of the output method for the files in the radiographic image capturing system 100 are different depending on the type of the console 3. Among files described as various files, the file related to the data used for the image processing and image correction often has a different policy related to image quality management (maintenance) for each manufacturer, and it is assumed that a calibration target for image quality management is different, or a calibration method is different even for the same target. Therefore, the generated file is different for each of the consoles 3. The controller 21 may perform control to hold a plurality of files related to the data used for the image processing and image correction as files attached to the console 3, switch a file to be output, and output the file. In addition, among the data stored in the radiographic image capturing device 2, the data to be encrypted or the encryption scheme between the console 3 and the radiographic image capturing device 2 may be different. In particular, in a case where the console 3 is of a manufacturer as a cooperation partner, switching the formats of various files and the communication specifications for transfer (which also include a file compression method and an image data thinning method) in accordance with specifications of the manufacturer as the cooperation partner reduces labor of the manufacturer as the cooperation partner, and is preferred by the manufacturer.

In the present embodiment, the settings of the output method for the files are switched depending on the console 3 to which the radiographic image capturing device 2 is connected, so that it is possible to maximize the unique function of the radiographic image capturing system 100 in which the radiographic image capturing device 2 is used.

Furthermore, the controller 21 performs control to switch the image processing method for an image captured by the radiographic image capturing device 2 depending on the console 3 to which the radiographic image capturing device 2 is connected. More specifically, for example, in a case where the plurality of consoles 3 have different settings of the image processing method in the radiographic image capturing system 100 and the console 3 to which the radiographic image capturing device 2 is connected is switched, the controller 21 performs control to switch the settings of the image processing method for the image captured by the radiographic image capturing device 2.

Examples of the settings of the image processing method include settings of a correction processing method in the radiographic image capturing system 100 and correction data used in the radiographic image capturing system 100.

The settings of the correction processing method include settings of an algorithm used for correction processing, settings of a device that performs the correction processing, and the like. The device that performs the correction processing is, for example, either the radiographic image capturing device 2 or the console 3. Types of the correction data include a gain, an offset parameter, an image deletion map, and the like.

The settings of the image processing method are appropriately changed according to, for example, an image capturing mode (image capturing, calibration, image quality priority, image capturing speed priority, or the like) in the radiographic image capturing system 100 or a policy of a manufacturer of each device.

In particular, regarding the correction processing method, whether the processing is performed by the radiographic image capturing device 2 or the console 3 or which algorithm is used may be different depending on the image capturing mode or the policy of the manufacturer. For example, if there is such a reason that the console 3 is equipped with a unique technique of image processing and image correction, which has superiority to other manufacturers, it is preferable that the radiographic image capturing device 2 perform processing before the image processing and image correction on an image and transmit the processed image to the console 3. Alternatively, in a case where a specific one of the consoles 3 includes an image quality priority mode, a speed priority mode, and the like as image capturing modes, it is conceivable to perform control such that all image quality processing is performed when the image quality priority mode is selected, and some image processing is skipped to provide a captured image for the user more quickly when the speed priority mode is selected. As for the correction data, contents of the correction data to be used may be different depending on the policy of the manufacturer. For example, the policy of the manufacturer may be a policy of creating correction data subdivided for each condition related to radiation irradiation, such as a tube voltage, a tube current, an irradiation time, and a current time product, or a policy of creating common correction data without subdivision. The image capturing conditions for generating the correction data may be different.

Thus, the image processing method is switched depending on the console 3 to which the radiographic image capturing device 2 is connected, so that it is possible to maximize the unique function of the radiographic image capturing system 100 in which the radiographic image capturing device 2 is used.

Furthermore, the controller 21 performs control to switch settings of the user interface depending on the console 3 to which the radiographic image capturing device 2 is connected. More specifically, for example, in a case where the plurality of consoles 3 have different settings related to the user interface in the radiographic image capturing system 100 (the radiographic image capturing device 2 and the console 3) and the console 3 to which the radiographic image capturing device 2 is connected is switched, the controller 21 performs control to switch the settings related to the user interface.

Examples of the settings related to the user interface include a method of notifying the user of various types of user notification information, a lighting pattern (notification pattern) of a lighting unit (not illustrated in FIGS. 2 and 3) in each device, a method of notifying the user of restriction or prohibition of an operation not supported by the system, and a method of notifying the user of the level of a power supply or a remaining battery capacity. Examples of the various types of user notification information include a method of notifying the user that the radiographic image capturing device 2 has been selected for image capturing, that image capturing is being prepared, or that image capturing is possible, and a method of notifying the user that image capturing cannot be performed due to an error caused by a drop, impact, or the like of the radiographic image capturing device 2. Since these notification methods have a uniform design by the manufacturer, it is preferable from the viewpoint of the user to operate in accordance with the uniform design.

Note that the user interface may be any interface, such as a display unit, a lighting unit, or a voice output unit, as long as the user can recognize information transmitted from the device in some form.

The settings related to the user interface are appropriately changed depending on the type of the console 3, the policy of the manufacturer of each device, or the like. For example, since contents of the system are different for each of the consoles 3 to which the radiographic image capturing device 2 is connected, it is necessary to notify the user which one of the radiographic image capturing systems 100 the radiographic image capturing device 2 is applied to so that the user does not erroneously recognize the system. The notification may be made to the console 3 or the radiographic image capturing device 2.

In addition, the settings related to the user interface include specifications for lighting of the lighting unit at the time of charging the battery, specifications for display of the remaining battery capacity, and lighting patterns of the lighting unit associated with functions unique to the manufacturer. Furthermore, there may be a common function and a non-common function depending on the radiographic image capturing system 100. Therefore, it is necessary to notify the user of a function not supported by the radiographic image capturing system 100.

In the present embodiment, the settings related to the user interface are switched depending on the console 3 to which the radiographic image capturing device 2 is connected, so that it is possible to maximize the unique function of the radiographic image capturing system 100 in which the radiographic image capturing device 2 is used.

Furthermore, the controller 21 performs control to switch settings related to the system depending on the console 3 to which the radiographic image capturing device 2 is connected. More specifically, for example, in a case where the plurality of consoles 3 have different settings related to the system in the radiographic image capturing system 100 and the console 3 to which the radiographic image capturing device 2 is connected is switched, the controller 21 performs control to switch the settings related to the system.

Examples of the settings related to the system include settings of an internet protocol (IP) address (static IP address or dynamic IP address) used in the system, settings of power supply linkage specifications of a peripheral device, settings of a quality control condition in the system, settings of an installation method in the system, and settings of a method of upgrading or downgrading the version of the software in the system.

The settings related to the system are appropriately changed depending on the type or the like of the console 3. For example, in the case of switching to a system that controls a power supply of the radiographic image capturing device 2 in synchronization with turning on or off of a power supply of the peripheral device, it is necessary to control the power supply according to the system.

In addition, according to the policy of the manufacturer, a management item and a management method for quality guarantee are different depending on the type of the console 3. For example, a timing of a periodic maintenance (once a week, once a month, or the like), a correction data acquisition sequence at the time of the periodic maintenance, and the type, format, algorithm, and the like of the correction data to be acquired are different.

In addition, the settings of the installation method such as settings of communication between the console 3 and the radiographic image capturing device 2 are different depending on the system. In addition, in a case where the radiographic image capturing device 2 moves among two or more systems, versions of the software defined as combined versions of the systems include the latest version and a version that is not the latest, depending on the system. Therefore, it is necessary to upgrade or downgrade the versions of the software according to the system to which the radiographic image capturing device 2 is applied.

In the present embodiment, the settings related to the system are switched depending on the console 3 to which the radiographic image capturing device 2 is connected, so that it is possible to maximize the unique function of the radiographic image capturing system 100 in which the radiographic image capturing device 2 is used.

Note that the radiographic image capturing device 2 may be able or unable to execute serial image capturing of a pulse irradiation type depending on the type of the generator 11, and thus, the controller 21 may control the operation of the radiographic image capturing device 2 depending on the type of the radiation irradiation device 1. Note that the serial image capturing means that the radiographic image capturing device 2 repeats accumulation of charges and reading of signal values a plurality of times in a short time based on one image capturing operation to obtain a series of a plurality of images.

In addition, in a case where a function of an operation unit of the controller 21 can be changed in each system, the controller 21 may switch the function of the operation unit depending on the type of the console 3.

Figure 4:
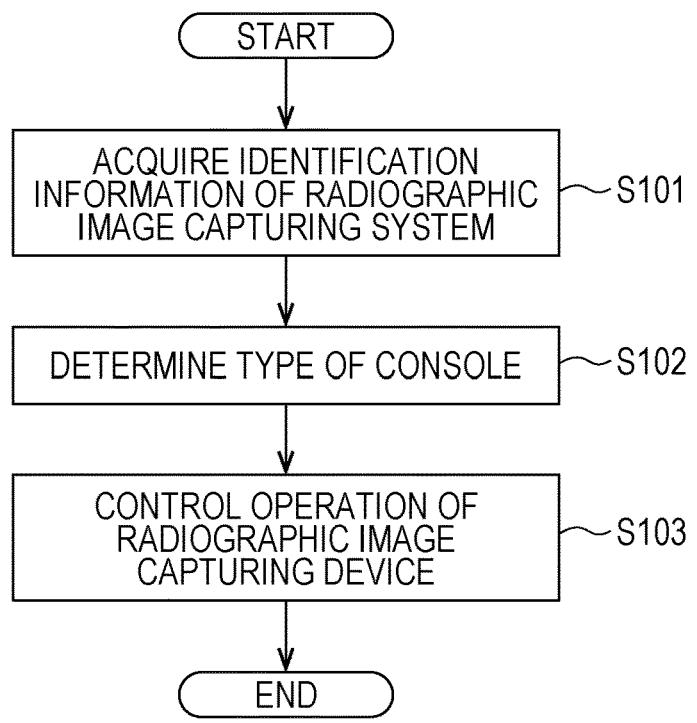
FIG. 4 is a flowchart illustrating an operation example of operation control of the radiographic image capturing device.

An operation example of operation control of the radiographic image capturing device 2 configured as described above will be described. FIG. 4 is a flowchart illustrating the operation example of the operation control of the radiographic image capturing device 2. The processing in FIG. 4 is appropriately executed, for example, when the radiographic image capturing device 2 is connected to the console 3 of a predetermined one of the radiographic image capturing systems 100.

As illustrated in FIG. 4, the controller 21 acquires the identification information of the radiographic image capturing system 100 (step S101). Next, the controller 21 determines the type of the console 3 (step S102). The controller 21 then controls the operation of the radiographic image capturing device 2 (step S103). Thereafter, this control ends.

Next, effects of the radiographic image capturing device 2 (the radiographic image capturing system 100) according to the present embodiment will be described.

For example, it is assumed that a radiographic image capturing system of the second manufacturer is introduced in a facility in which a radiographic image capturing system of the first manufacturer is introduced. In a case where a plurality of radiographic image capturing systems having different specifications coexist in the same facility, a radiographic image capturing system can be appropriately selected according to convenience of an image capturing work. Thus, it is thought that a radiographic image capturing work can be flexibly operated, and the convenience for the user is improved.

In this case, if a radiographic image capturing device having specifications of the first manufacturer, which is originally introduced in the facility, can be applied to the radiographic image capturing system of the second manufacturer, the radiographic image capturing device can be shared among the radiographic image capturing systems, so that the cost can be suppressed as a whole.

However, if the radiographic image capturing device according to the first manufacturer is connectable to the first console according to the first manufacturer but is not connectable to the second console according to the second manufacturer, the radiographic image capturing system according to the first console can perform the image capturing operation but the radiographic image capturing system according to the second console cannot perform the image capturing operation.

Thus, the radiographic image capturing device cannot be shared in the facility in which the first console and the second console coexist. Therefore, it is necessary to separately purchase a radiographic image capturing device connectable to the second console, which is costly.

On the other hand, in the present embodiment, since it is possible to connect the radiographic image capturing device 2 to the plurality of types of consoles 3 having different specifications, one radiographic image capturing device 2 can be easily shared in a facility in which a plurality of radiographic image capturing systems having a plurality of types of consoles having different specifications coexist.

As a result, moving one radiographic image capturing device 2 among the systems makes it possible to easily capture a radiographic image by use of a radiographic image capturing system according to the convenience of an image capturing work.

That is, in the present embodiment, it is not necessary to separately purchase radiographic image capturing devices dedicated to the consoles, so that the overall cost can be reduced. As a result, it is possible to improve the convenience for the user.

In addition, even a radiographic image capturing device connectable to a plurality of types of consoles may not be compatible with respective functions of the plurality of types of consoles. In this case, a basic image capturing operation in a radiographic image capturing system can be performed, but, in the radiographic image capturing system in which the radiographic image capturing device is not compatible with a function of the console, the function unique to the system cannot be used. For example, in a case where the radiographic image capturing device cannot apply to settings of an image processing method of the radiographic image capturing system to which the radiographic image capturing device is connected, it is not possible to generate a desired image in the radiographic image capturing system.

Therefore, it is difficult for a user who wants to use the function of the radiographic image capturing system to obtain the advantage of using the radiographic image capturing system.

On the other hand, in the present embodiment, the radiographic image capturing device 2 is configured to be compatible with the respective functions of the plurality of types of consoles 3, and thus can change settings of a function according to the console 3 to which the radiographic image capturing device 2 is connected.

As a result, using one radiographic image capturing device 2 makes it possible to fully utilize the functions of the plurality of types of radiographic image capturing systems 100, so that it is possible to further improve the convenience for the user.

Furthermore, since the radiographic image capturing device 2 according to the present embodiment is connectable to the plurality of types of consoles 3 and is compatible with the functions of the plurality of types of consoles 3, the radiographic image capturing device 2 is easily adapted to a facility in which a plurality of types of radiographic image capturing systems (consoles) are introduced. Therefore, the facility can achieve cost reduction by introducing the radiographic image capturing device 2 according to the present embodiment, and can enjoy advantages of the plurality of types of radiographic image capturing systems.

In addition, the manufacturer of the console 3 can facilitate introduction of his radiographic image capturing system (console) into a facility in which a radiographic image capturing system to which the radiographic image capturing device 2 of another manufacturer is applied is introduced, for example. As a result, the relationship between the manufacturers can be strengthened, and thus a synergy effect between the manufacturers can be easily exhibited.

Note that, in the above embodiment, the controller 21 of the radiographic image capturing device 2 controls the operation of the radiographic image capturing device 2, but the present invention is not limited thereto. For example, the image capturing controller of the console may control the operation of the radiographic image capturing device, or a controller of an external device may control the operation of the radiographic image capturing device.

Figure 5:
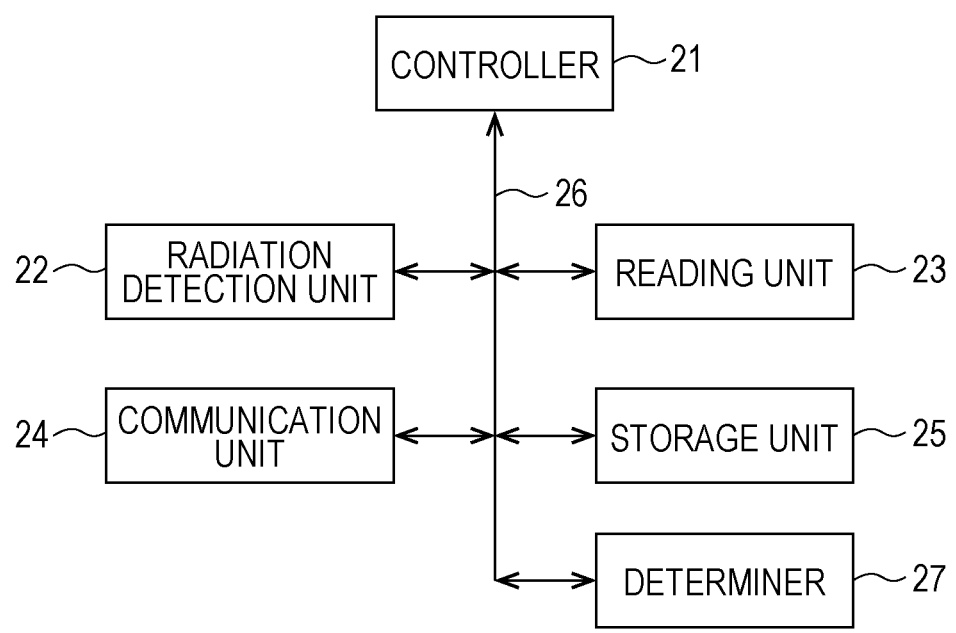
FIG. 5 is a block diagram illustrating a configuration of a radiographic image capturing device according to a modification.

In the above embodiment, the determiner is incorporated in the controller of the radiographic image capturing device, but the present invention is not limited thereto. As illustrated in FIG. 5, a determiner 27 may be provided separately from the controller 21 of the radiographic image capturing device 2.

In addition, the above embodiment is merely an example of implementation in carrying out the present invention, and the technical scope of the present invention should not be interpreted in a limited manner by this embodiment. That is, the present invention can be carried out in various forms without departing from its gist or its main features.

Although embodiments of the present invention have been described and illustrated in detail, the disclosed embodiments are made for purposes of illustration and example only and not limitation. The scope of the present invention should be interpreted by terms of the appended claims

What is claimed is:

1. A radiographic image capturing device connectable to a plurality of types of radiographic image capturing control devices having different manufacturer, the radiographic image capturing device comprising:
   a hardware processor that
      acquires information indicating a type of a radiographic image capturing control device connected to the radiographic image capturing device;
      determines one type of radiographic image capturing control device among the plurality of types of radiographic image capturing control devices based on the acquired information; and
      controls the operation of the radiographic image capturing device based on a determination result of the hardware processor, wherein
   the hardware processor
      performs control to switch an image capturing method of the radiographic image capturing device based on the determination result of the hardware processor, the image capturing method being an irradiation cooperation method between the radiographic image capturing device and a radiographic irradiation device;
      performs an irradiation cooperation by hardware with a radiographic irradiation device connected to the radiographic image capturing control device of a first manufacturer; and
      performs an irradiation cooperation by software with a radiographic irradiation device connected to the radiographic image capturing control device of a second manufacturer.

2. The radiographic image capturing device according to claim 1, wherein
   the information indicating the type of the radiographic image capturing control device is at least one of information related to a manufacturer of the radiographic image capturing control device, information related to a model of the radiographic image capturing control device, or information related to software used in the radiographic image capturing control device.

3. The radiographic image capturing device according to claim 1, wherein
   the hardware processor performs control to switch error processing in image capturing of the radiographic image capturing device or settings related to the error processing.

4. The radiographic image capturing device according to claim 1, wherein
   the hardware processor switches an image processing method for an image captured by the radiographic image capturing device based on the determination result of the hardware processor.

5. The radiographic image capturing device according to claim 1, wherein
   the hardware processor switches an output method for a file based on the determination result of the hardware processor.

6. The radiographic image capturing device according to claim 1, wherein
   the hardware processor switches settings related to a user interface based on the determination result of the hardware processor.

7. The radiographic image capturing device according to claim 1, wherein
   the radiographic image capturing device is compatible with respective functions of the plurality of types of radiographic image capturing control devices.

8. The radiographic image capturing device according to claim 1, wherein
   each of the plurality of types of radiographic image capturing control devices is connected to a different one of plurality of radiation irradiation devices.

9. The radiographic image capturing device according to claim 3, wherein
   in the error processing, at least one of a type of error content, a logic of error determination, a threshold of error determination, and error output specification is different depending on the plurality of types of radiographic image capturing control devices having different manufacturer.

10. The radiographic image capturing device according to claim 4, wherein
    the hardware processor switches correction data to be used in image processing.

11. The radiographic image capturing device according to claim 5, wherein
    the hardware processor switches settings of a format of the file.

12. The radiographic image capturing device according to claim 5, wherein
    the hardware processor switches information to be encrypted or an encryption scheme of information stored in the radiographic image capturing device.

13. The radiographic image capturing device according to claim 6, wherein
    the hardware processor switches settings of a notification pattern related to the user interface.

14. The radiographic image capturing device according to claim 6, wherein
    the hardware processor switches settings of a method of notifying a user of various types of user notification information related to the user interface.

15. The radiographic image capturing device according to claim 6, wherein
    the hardware processor switches a method of notifying a user of a level of a power supply or a remaining battery capacity related to the user interface.

16. A radiographic image capturing system comprising:
a radiographic image capturing device connectable to a plurality of types of radiographic image capturing control devices having different manufacturer; and one of the plurality of types of radiographic image capturing control devices, wherein
the radiographic image capturing device includes a hardware processor that
acquires information indicating a type of a radiographic image capturing control device connected to the radiographic image capturing device;
determines one type of radiographic image capturing control device among the plurality of types of radiographic image capturing control devices based on the acquired information; and
controls the operation of the radiographic image capturing device based on a determination result of the hardware processor, wherein
the hardware processor
performs control to switch an image capturing method of the radiographic image capturing device based on the determination result of the hardware processor, the image capturing method being an irradiation cooperation method between the radiographic image capturing device and a radiographic irradiation device;
performs an irradiation cooperation by hardware with a radiographic irradiation device connected to the radiographic image capturing control device of a first manufacturer; and
performs an irradiation cooperation by software with a radiographic irradiation device connected to the radiographic image capturing control device of a second manufacturer.

17. The radiographic image capturing system according to claim 16, wherein
the hardware processor notifies a user of a restriction or prohibition of an operation not supported by a system including the radiographic image capturing device and the radiographic image capturing control device connected to the radiographic image capturing device.

18. A radiographic image capturing device connectable to a plurality of types of radiographic image capturing control devices having different manufacturer, the radiographic image capturing device comprising:
a hardware processor that
acquires information indicating a type of the radiographic image capturing control device connected to the radiographic image capturing device;
determines one type of radiographic image capturing control device among the plurality of types of radiographic image capturing control devices based on the acquired information; and
controls the operation of the radiographic image capturing device based on a determination result of the hardware processor, wherein
the hardware processor
switches settings related to a radiographic image capturing system based on the determination result of the hardware processor, the radiographic image capturing system including a radiographic image capturing control device that is connected to the radiographic image capturing device; and
sets, depending on the plurality of types of radiographic image capturing control devices having different manufacturer, at least one of an internet protocol (IP) address used in the system, power supply linkage specifications of a peripheral device, a quality control condition in the system, a method of upgrading or downgrading version of a software in the system.

19. The radiographic image capturing device according to claim 18, wherein
the hardware processor sets a static IP address as the IP address when the radiographic image capturing device is connected to the radiation image capturing control device of a first manufacturer; and sets a dynamic IP address as the IP address when the radiographic image capturing device is connected to the radiation image capturing control device of a second manufacturer.

20. A radiographic image capturing system comprising:
a radiographic image capturing device connectable to a plurality of types of radiographic image capturing control devices having different manufacturer; and one of the plurality of types of radiographic image capturing control devices, wherein
the radiographic image capturing device includes a hardware processor that
acquires information indicating a type of a radiographic image capturing control device connected to the radiographic image capturing device;
determines one type of radiographic image capturing control device among the plurality of types of radiographic image capturing control devices based on the acquired information; and
controls the operation of the radiographic image capturing device based on a determination result of the hardware processor, wherein
the hardware processor
switches settings related to a radiographic image capturing system based on the determination result of the hardware processor, the radiographic image capturing system including a radiographic image capturing control device that is connected to the radiographic image capturing device; and
sets, depending on the plurality of types of radiographic image capturing control devices having different manufacturer, at least one of an internet protocol (IP) address used in the system, power supply linkage specifications of a peripheral device, a quality control condition in the system, a method of upgrading or downgrading version of a software in the system.

\* \* \* \* \*